United States Patent [19]
Fujiwara et al.

[11] Patent Number: 5,981,510
[45] Date of Patent: Nov. 9, 1999

[54] METHOD FOR TREATING AND IMPROVING DIABETES

[75] Inventors: Michio Fujiwara, Tokyo; Seisuke Inada, Kashiwazaki; Yoshiharu Matahira, Shimada; Shigehiro Kaneko, Sendai, all of Japan

[73] Assignee: Yaizu Suisankagaku Industry Co., Ltd., Yaizu, Japan

[21] Appl. No.: 09/060,381

[22] Filed: Apr. 15, 1998

[30] Foreign Application Priority Data

Apr. 15, 1997 [JP] Japan ................................. 9-113346
Jul. 9, 1997 [JP] Japan ................................. 9-199370

[51] Int. Cl.⁶ ................................................ A01N 43/04
[52] U.S. Cl. ................................. 514/62; 514/61; 514/62
[58] Field of Search .............................. 514/55, 866, 61, 514/62

[56] References Cited

FOREIGN PATENT DOCUMENTS

| | | |
|---|---|---|
| 59-43949 | 10/1984 | Japan . |
| 1-258623 | 10/1989 | Japan . |
| 4-124139 | 4/1992 | Japan . |
| 4-178381 | 6/1992 | Japan . |
| 4-210977 | 8/1992 | Japan . |
| 5-86399 | 12/1993 | Japan . |
| 6-321787 | 11/1994 | Japan . |
| 7-206673 | 8/1995 | Japan . |
| 7-228539 | 8/1995 | Japan . |

*Primary Examiner*—Howard C. Lee
*Attorney, Agent, or Firm*—Smith, Gambrell & Russell; Beveridge, DeGrandi, Weilacher & Young

[57] ABSTRACT

A method for treating and improving diabetes and liver dysfunction, can be obtained by administering at least one selected from a chitin oligosaccharide, a chitosan oligosaccharide and salts thereof, in an effective amount. As the chitin oligosaccharide, preferred is one having the degree of polymerization of from 2 to 7. As the chitosan oligosaccharide, preferred is one having the degree of polymerization of from 2 to 8. As the method for administration, it is preferred to add them to e.g. foods, medicines or feeds, and orally ingest them. However, when used as medicines, administration methods such as intravenous injection and muscular injection, may be used.

2 Claims, 11 Drawing Sheets

Change of blood glucose level

Change of body weight

Change of ingested amount of feed

Change of ingested amount of water

Blood glucose level

Body weight

Ingested amount of feed

Ingested amount of water

METHOD FOR TREATING AND IMPROVING DIABETES

BACKGROUND OF THE INVENTION

The present invention relates to a method for preventing and improving diabetes and liver dysfunction.

In recent years, in Japan, reflecting the progressive increasing in elderly population and the westernization of diet, the incidence of various deseases of adult people has increased. Among them, diabetes is a generic term of chronic high blood glucose and various complications (such as retinopathy, neuropathy, nephropathy and immune disorder) induced by capillary dysfunction accompanying the chronic high blood glucose, and it is estimated that domestically about five million patients are suffering from them. Diabetes is generally classified into insulin dependent diabetes mellitus (IDDM) and non insulin dependent diabetes mellitus (NIDDM). In Japan, it is reported that IDDM patients account for at most 5%, while NIDDM patients account for at least 95%. Particularly, NIDDM which is related to habitat factors such as obesity, overfeeding, ataxia and senescence, is expected to increase in the future in Japan where the progressive increasing in elderly population and the westernization of diet, will further advance.

As the causes of IDDM, it is generally known that viral infection or defects of autoimmunization mechanism causes inflammation of Langerhaus islet of pancreas, resulting in the destruction of beta-cells as the insulin-producing cells, whereby insulin will not be secreted to develop IDDM. Accordingly, treatment is made by administration of insulin.

Further, as the causes of NIDDM, it is believed that although insulin is secreted, the action of insulin on cells is inadequate, whereby the cells can not take glucose in the blood sufficiently and a hyperglycemia state is thereby continued. Accordingly, for the treatment, insulin is not necessarily required and dietary treatment and excercise treatment are mainly used.

If the hyperglycemia state is continued by diabetes, systemic capillary will fall into disorder and arteriosclerosis will advance, thereby causing obstruction of blood vessels in heart or brain and gangrene of legs. Further, if the blood glucose level is high, glucose in the blood is likely to bond to proteins in hemoglobin or tissues, whereby the functions thereof will be inhibited. As the results, complications such as retinopathy, nephropathy, neurosis, cerebral infarction, myocardinal infarction and cataract, are occurred. Further, since immunization power is decreased by diabetes, the patients are likely to catch infections easily.

If the complications become worse, recovery is very hard, and it is thereby important for the patients of diabetes to control the blood glucose level so that it will not rise above such level that no symptom is observed. For such a purpose, various antidiabetic agents such as hypoglycemic agents have heretofore been developed. For example, there may be mentioned, as natural materials, a hypoglycemic agent containing as an active ingredient, tea lactone as a water-soluble polysaccharide component of tea leaves (Japanese Unexamined Patent Publication No. 4-124139), an antidiabetic agent containing as an active ingredient, a hot water extracted fraction of banaba leaves (Japanese Unexamined Patent Publication No. 7-228539), a hypoglycemic agent of a xanthone extracted and isolated from Japanese green gentian (Japanese Unexamined Patent Publication No. 7-206673), and the like; and as chemically synthesized products, a moranolin N-substituted derivative (Japanese Examined Patent Publication No. 59-43949), a thiazolidine compound (Japanese Unexamined Patent Publication No. 4-210977) and a condensed 7-membered cyclic compound having an imidazolyl group (Japanese Unexamined Patent Publication No. 4-178381), and the like.

The chemically synthesized products generally exhibit potent effects, but give unwanted side effects, whereby a long term administration accompanies many problems. While the natural extracted products are high in the safety, but mostly exhibit no adequate effects.

On the other hand, with respect to liver dysfunction as other one of the deseases of adult people, the degree can be grasped by indices such as COT or GPT in biochemical inspections of, for example, periodical medical checkup, and it has become easy to find disorders.

Liver plays important rolls in vivo, for example, detoxication, metabolism or storage of sugar, protein or lipid, and hormone control. Dysfunction of liver often leads to fatal results for living bodies. It is well known that the causes of liver dysfunction represented by hepatitis, are based on the habit of life, for example, over ingestion of alcoholic beverages, heavy drinking, heavy eating, irregular life or stress. However, it has been found that the liver dysfunction is often caused by hepatitis virus. Especially, if viral hepatitis becomes chronic, it will often become hepatic carcinoma through liver cirrhosis, whereby suitable preventing and improving method has been demanded.

Many proposals have heretofore been made as a preventing and improving agent for hepatitis. However, chemically synthesized products generally exhibit potent effects, but have side effects, thereby being problematic for a long term administration, while natural extracted products are mostly high in the safety, but exhibit no adequate effects.

SUMMARY OF THE INVENTION

It is an object of the present invention to provide a method for preventing and imiproving diabetes which is high in the safety and gives adequate effects for reducing blood glucose.

It is another object of the present invention to provide a method for preventing and improving liver dysfunction which is high in the safety and gives adequate effects.

To accomplish the above objects, one aspect of the present invention is to provide a method for preventing and improving diabetes which comprises administering at least one selected from the group consisting of a chitin oligosaccharide, a chitosan oligosaccharide and salts thereof, in an effective amount.

Another aspect of the present invention is to provide a method for preventing and improving liver dysfunction which comprises administering at least one selected from the group consisting of a chitin oligosaccharide, a chitosan oligosaccharide and salts thereof, in an effective amount.

According to the present invention, as indicated in the test examples as shown below, with respect to mice of non insulin dependent diabetes mellitus which, have abnormality in the central nervous system for appetite and undergo remarkable obesity by over eating, significant effects on the reduction of the blood glucose can be observed.

Accordingly, it is expected to show preventing and improving effects against, especially the non insulin dependent diabetes mellitus of animals inclusive of humans.

Further, as indicated in the test examples as shown below, with respect to mice suffering from an artificially induced hepatitis, significant preventing and improving effects i.e. lessening the symptom, can be observed. Accordingly, it is expected to show a hyperglycemia improving effect or effects on preventing and improving liver dysfunction accompanying hepatitis or the like to animals inclusive of humans.

The chitin oligosaccharide, chitosan oligosaccharide and salts thereof used for these methods are obtained from polysaccharides as starting materials present abundantly in nature, and thereby are high in the safety and can be produced by relatively simple steps, such being advantageous in production costs.

Further, the chitin oligosaccharide, chitosan oligosaccharide and salts thereof are easily dissolved in water, whereby they are easily handled, and readily ingested in daily life by adding them to e.g. foods and drinks.

BRIEF EXPLANATION OF THE DRAWINGS

FIG. 9($b$) is a microscopic photograph showing a liver tissue of a mouse of a control group in an experiment of induced hepatitis using mice, with magnification of 400 times.

FIG. 10($b$) is a microscopic photograph showing a liver tissue of a mouse of a group to which a chitin oligosaccharide mixture was administered in an experiment of induced hepatitis using mice, with magnification of 400 times.

FIG. 11($b$) is a microscopic photograph showing a liver tissue of a mouse of a group to which a chitosan oligosaccharide acetate mixture was administered in an experiment of induced hepatitis using mice, with magnification of 400 times.

PREFERED EMBODIMENTS OF THE INVENTION

Figure 1:
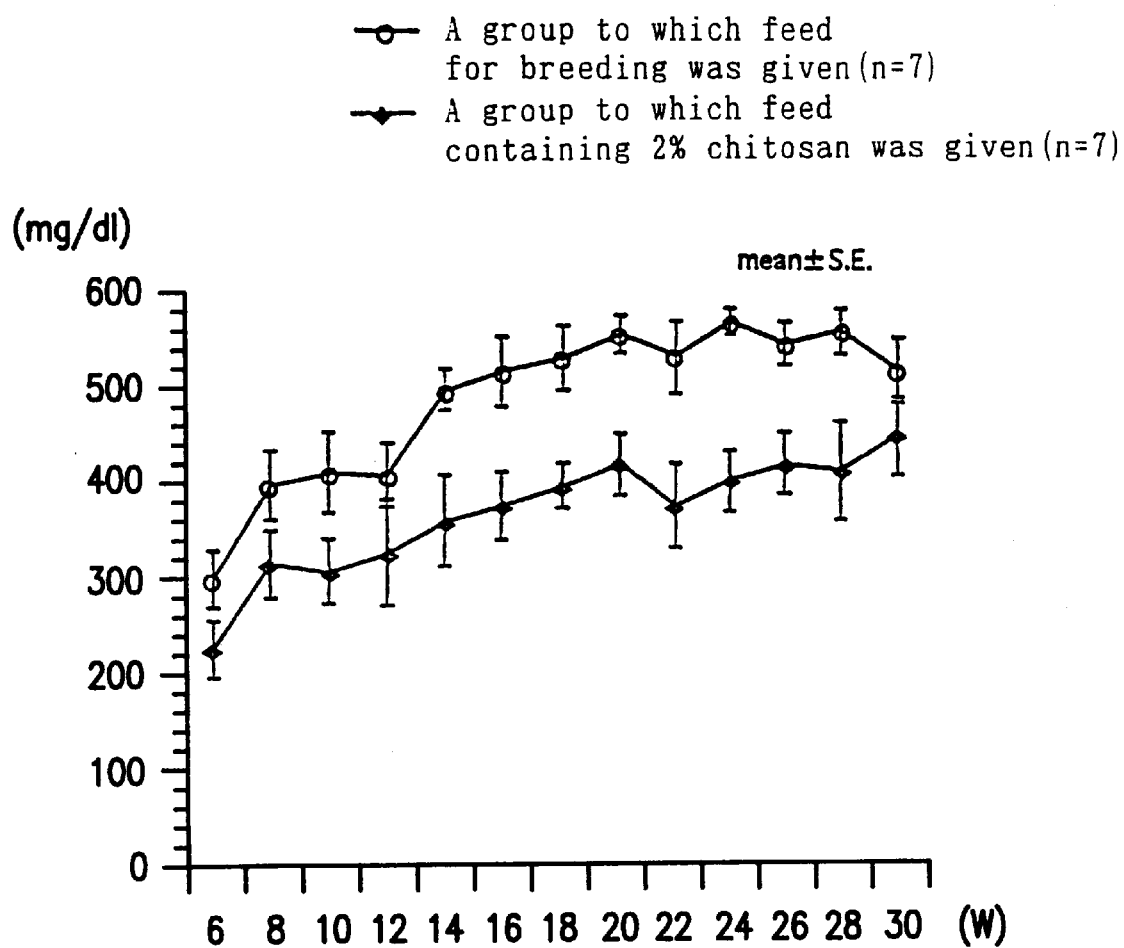
FIG. 1 is a graph showing the change of the blood glucose level in Test Example 1 wherein the effects of chitosan administration on the non insulin dependent diabetes mellitus of mice were examined.

Now, the present invention will be explained in further detail with reference to preferred embodiments.

The chitin oligosaccharide, chitosan oligosaccharide and salts thereof used in the present invention are obtained by chemically or biochemically treating chitin which is prepared from, for example, shells of crustaceans such as crab, lobster or shrimp by a conventional method.

Namely, the chitin oligosaccharide is obtained by subjecting chitin to partial hydrolysis with an acid or an enzyme, and if the case requires, fractionating or purifying the one with the desired degree of polymerization from the hydrolyzate by a method such as column chromatography or solvent fractionation. As the method of hydrolysis with an acid, for example, a method described in Japanese Examined Patent Publication No. 5-86399 by the present applicant, may preferably be used. As the degree of polymerization of the chitin oligosaccharide, preferred are ones at a level of from disaccharide to heptasaccharide, i.e. N-acetylchitobiose, N-acetylchitotriose, N-acetylchitotetrose, N-acetylchitopentose, N-acetylchitohexose and N-acetylchitoheptose. Among them, one or a mixture of at least two of them may preferably be used. In this connection, the chitin oligosaccharide or its mixture is commercially sold by the companies in this field, and, for example, "NA-COS-Y" (trade name, manufactured by Yaizu Suisan Kagaku Kogyo Kabushiki Kaisha) may be used.

The chitosan oligosaccharide is obtained by partially hydrolyzing chitosan which is obtained by subjecting chitin to a hot concentrated alkali treatment. The partial hydrolysis of chitosan is carried out by, for example, a method wherein, chitosan is heated together with an acid such as hydrochloric acid, acetic acid or formic acid, and then the acid is removed or nuetralization and desalting are conducted, followed by e.g. crystallization to form a powder, or a method wherein chitosan is dissolved in a dilute acid, and then, for example, chitosanase or D-glucosaminidase is allowed to react thereto. The degree of polymerization of the chitosan oligosaccharide obtained by such a method, is usually at a level of from disaccharide to octasaccharide, i.e. mixtures of e.g. chitobiose, chitotriose, chitotetrose, chitopentose, chitohexose, chitoheptose and chitooctose. In the present invention, it is possible to use the chitosan oligosaccharides in the mixture state as mentioned above. However, it is also possible to subject such a mixture to fractionation and purification to obtain the one having the desired degree of polymerization by a method such as column chromatography or solvent fractionation. In this connection, the chitosan oligosaccharide or its mixture is commercially sold by the companies in this field, and, for example, "COS-Y" (trade name, manufactured by Yaizu Suisan Kagaku Kogyo Kabushiki Kaisha) may be used.

Further, in the present invention, as the salts of the chitin oligosaccharide and chitosan oligosaccharide, inorganic acid salts such as hydrochlorides and sulfates, and organic acid salts such as acetates, lactates and formates, may, for example, preferably be used.

The method for preventing and improving diabetes or liver dysfunction of the present invention, is characterized by administering at least one selected from the group consisting of a chitin oligosaccharide, a chitosan oligosaccharide and salts thereof, in an effective amount. The method for preventing and improving diabetes or liver dysfunction of the present invention, can be applied to not only humans but also various animals such as pets or livestock. As the method for administration, it is preferred to add at least one selected from the group consisting of a chitin oligosaccharide, a chitosan oligosaccharide and salts thereof, to e.g. foods, medicines or feeds, and orally ingest them. However, when used as medicines, administration methods such as intravenous injection and muscular injection, may be applied. Since the chitin oligosaccharide, chitosan oligosaccharide and salts thereof are readily dissolved in water, the addition to e.g. foods, medicines or feeds, can easily be made.

In the method for preventing and improving diabetes of the present invention, the dose of the chitin oligosaccharide, chitosan oligosaccharide or salts thereof, may vary depending upon e.g. the types of animals (inclusive of humans), administration periods, or the types of the e.g. foods, medicines or feeds to be incorporated. However, it is preferred to administer as the chitin oligosaccharide or chitosan oligosaccharide, 0.1 to 3,000 mg in the case of oral administration, from 0.01 to 1,000 mg in the case of intravenous injection, and from 0.01 to 1,000 mg in the case of muscular injection, per kg of the body weight. Further, the incorporated amount to e.g. foods, medicines and feeds, is preferably from 0.01 to 10 wt %.

Likewise, in the method for preventing and improving liver dysfunction of the present invention, the dose of the chitin oligosaccharide, chitosan oligosaccharide or salts thereof, is preferably, as the chitin oligosaccharide or chitosan oligosaccharide, 0.1 to 1,000 mg in the case of oral administration, from 0.01 to 100 mg in the case of intravenous injection, and from 0.01 to 100 mg in the case of muscular injection, per kg of the body weight. Further, the incorporated amount to e.g. foods, medicines and feeds, is preferably from 0.01 to 10 wt %.

The safeties of the chitin oligosaccharide and chitosan oligosaccharide have already been confirmed. For example, results of acute toxicity tests show that the safeties of both polysaccharides are LD50>5g/kg in the case of oral administration of rats.

Hereinafter, the present invention will be described in further detail with reference to examples. However, it should be understood that the present invention is by no means restricted by them.

EXAMPLE 1

(Preparation of a Chitin Oligosaccharide Mixture)

To 1,000 g of chitin derived from shells of crab, 4,000 ml of 12N hydrochloric acid was added. Stirring was conducted in a water bath at 45° C. for 3 hours, and then 4,000 ml of water was added thereto and the reaction was terminated. After neutralization to pH6.0 with 25% caustic soda, decoloring with activated carbon, filtration and desalting by electrodialysis were conducted. After purification by a treatment with ion exchange resins, spray drying was conducted to obtain 420 g of a chitin oligosaccharide mixture.

The composition of this chitin oligosaccharide mixture was 35 wt % of N-acetylglucosamine, 19 wt % of N-acetylchitobiose, 15 wt % of N-acetylchitotriose, 12 wt % of N-acetylchitotetrose, 8 wt % of N-acetylchitopentose, 6 wt % of N-acetylchitohexose and 5 wt % of N-acetylchitoheptose.

EXAMPLE 2

(Preparation of a Chitosan Oligosaccharide Mixture)

To 100 g of chitosan derived from shells of crab, 400 ml of 12N hydrochloric acid was added. Stirring was conducted in a water bath at 70° C. for 2 hours, and then 400 ml of water was added thereto and the reaction was terminated. Insolubles were removed by filtration with a filter. Then, 10 g of activated charcoal was added and stirring was conducted for 1 hour, followed by filtration with a filter for removal of activated charcoal to obtain 700 ml of a separated and decolored liquid. This separated and decolored liquid was concentrated under reduced pressure while distilling hydrochloric acid off. To the obtained syrup-like condensate, 300 ml of methanol was added and further 900 ml of acetone was added, to deposit a crystalline precipitate. This precipitate was collected by filtration with a filter, and dried in vacuum to obtain 120 g of a chitosan oligosaccharide mixture.

The glucose composition of this chitosan oligosaccharide mixture was 32 wt % of glucosamine, 20 wt % of chitobiose, 14 wt % of chitotriose, 14 wt % of chitotetrose, 10 wt % of chitopentose, 4 wt % of chitohexose, 4 wt % of chitoheptose and 2 wt % of chitooctose.

EXAMPLE 3

(Preparation of a Chitosan Oligosaccharide Acetate Mixture)

To 250 g of chitosan derived from shells of crab, 5 liters of water and 90 g of glacial acetic acid were added, followed by stirring one night to obtain a viscous solution. To this chitosan solution, 50 mg of chitosanase (manufactured by Meiji Seika Kabushiki Kaisha) derived from *Bachillus pumilus* was added, and stirring was conducted in a water bath at 40° C. for 18 hours. After the completion of the reaction, heating was conducted at 80° C. for 10 minutes to deactivate the enzyme, to obtain a chitosan oligosaccharide solution. Then, the chitosan oligosaccharide solution was spray dried to obtain 210 g of a chitosan oligosaccharide acetate mixture.

The glucose composition of this chitosan oligosaccharide acetate mixture was 25 wt % of chitobiose acetate, 24 wt % of chitotriose acetate, 19 wt % of chitotetrose acetate, 16 wt % of chitopentose acetate, 8 wt % of chitohexose acetate, 5 wt % of chitoheptose acetate and 3 wt % of chitooctose acetate.

TEST EXAMPLE 1

(Effects of Chitosan Administration on Mice of Induced NIDDM)

Firstly, for comparison, effects of chitosan as a polysaccharide on mice suffering from diabetes were examined. As a model mouse of diabetes, C57BL/KsJ db/db mouse (hereinafter referred to as "db mouse") was used. It is known that this mouse has abnormality in the central nervous system for appetite and shows obesity by over eating in an early stage, whereby NIDDM accompanying a high blood glucose tends to occur.

To the db mice (n=7), a commercially available feed for breeding (trade name "CE-2", manufactured by Nippon Clea) to which 2 wt % of chitosan was blended, was given from the age of 4 weeks old. To the db mice (n=7) of a control group, the same feed containing no chitosan was given. For each of these mice, the blood glucose level was measured every two weeks, and the average body weight and the average ingested amounts of the feed and water were measured every week. The blood glucose level was measured by a hexonase test paper method using "Titex" (trade name, manufactured by Ono Pharmaceutical K.K.).

Figure 2:
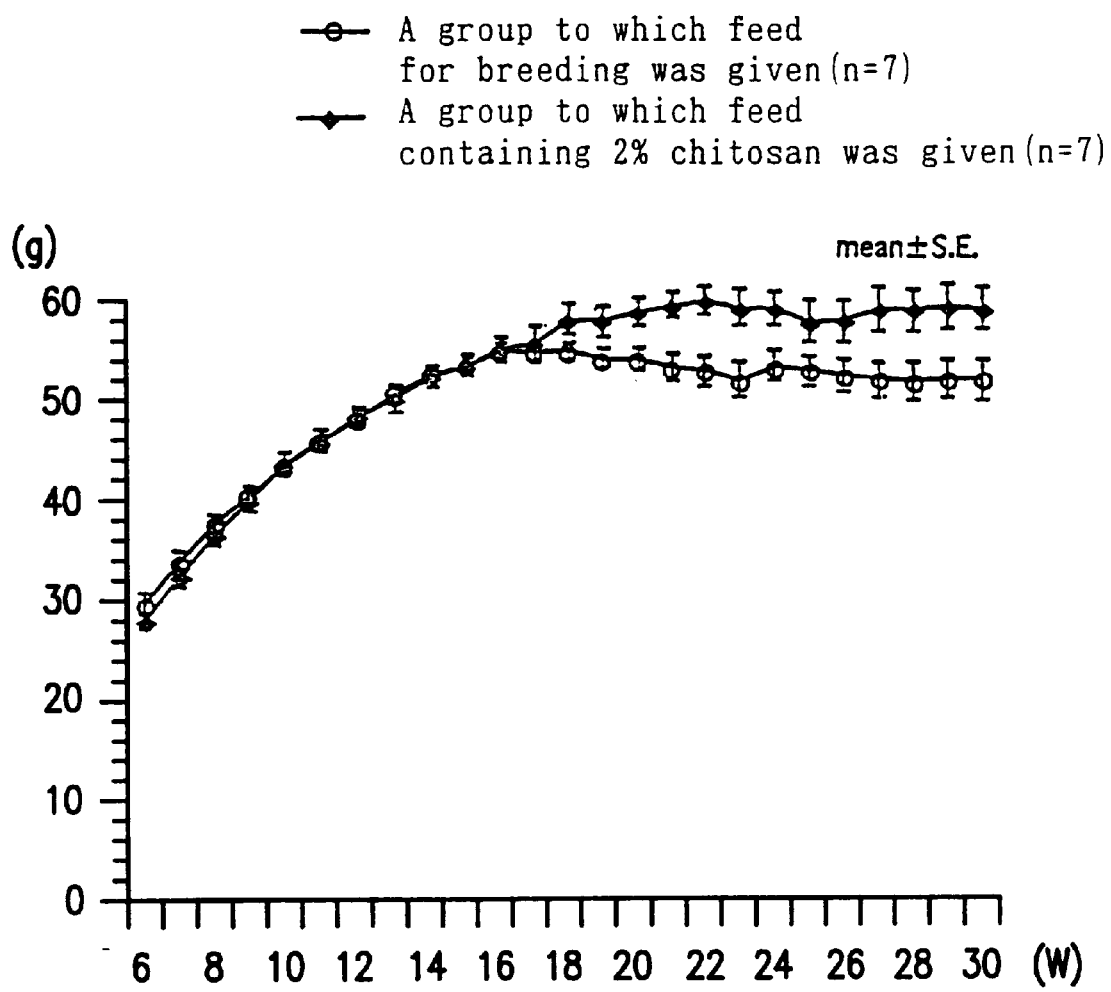
FIG. 2 is a graph showing the change of the body weight in Test Example 1.
Figure 3:
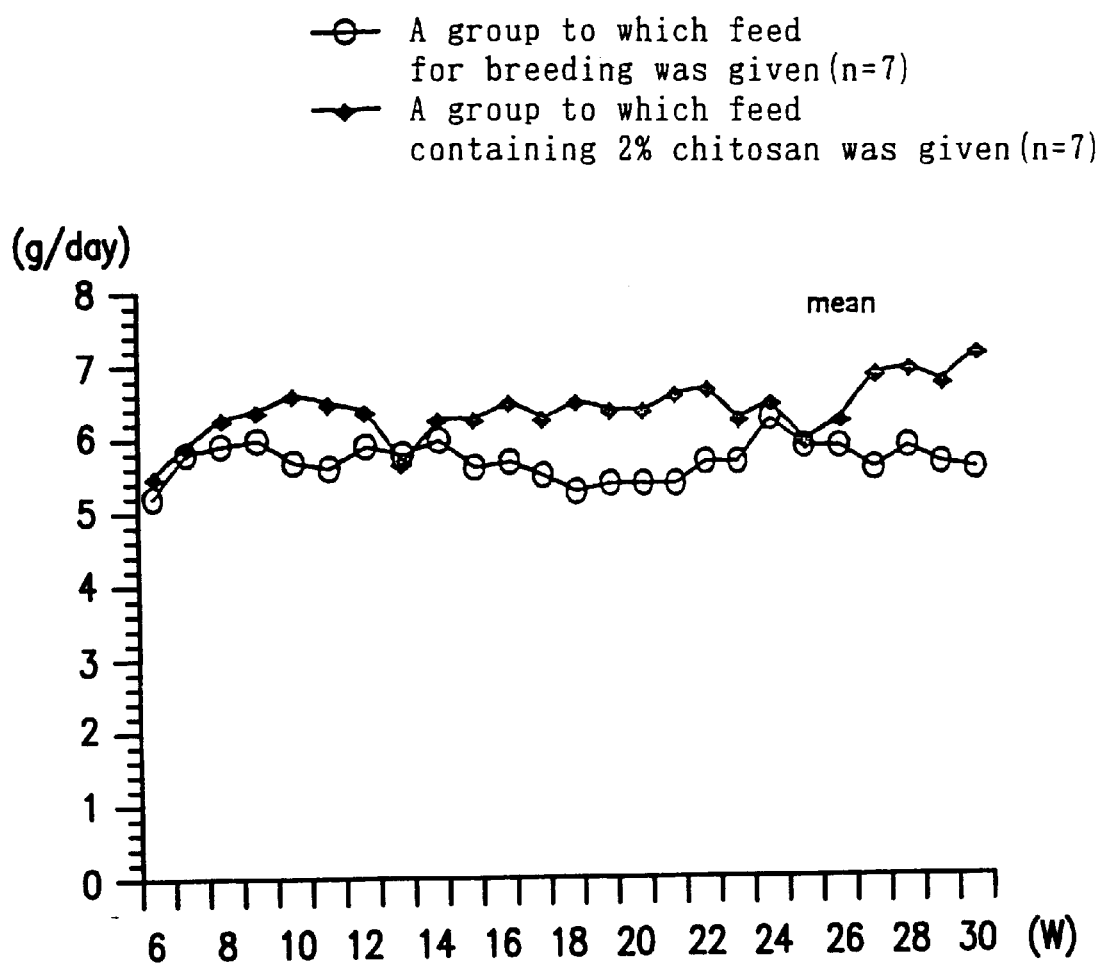
FIG. 3 is a graph showing the change of the ingested amount of feed in Test Example 1.
Figure 4:
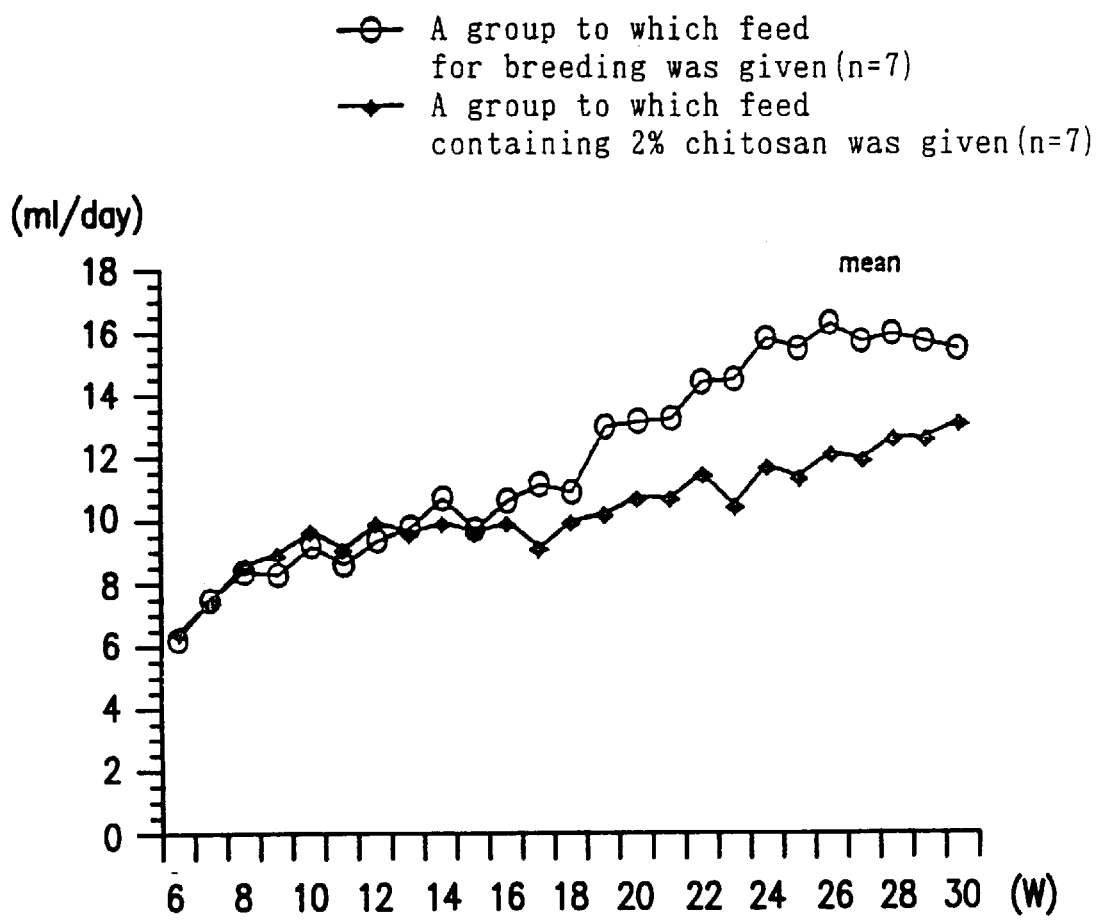
FIG. 4 is a graph showing the change of the ingested amount of water in Test Example 1.

As the results of the above tests, FIG. 1 shows the change of the blood glucose level, FIG. 2 shows the change of the average body weight, and FIGS. 3 and 4 show the change of the average ingested amounts of the feed and water, respectively. According to the results, in the blood glucose level, the average body weight and the average ingested amount of water, the chitosan-ingesting group tend to reduce as compared with the control group. Nevertheless, statistically, no significance was admitted.

TEST EXAMPLE 2

(Effects of Chitin Oligosaccharide or Chitosan Oligosaccharide Administration on Mice of Induced NIDDM)

To db mice of 8 weeks old, a commercially available feed for breeding "CE-2" was given as used in TEST EXAMPLE 1. To one group of the mice (n=18), water containing 0.5 wt % of the chitin oligosaccharide prepared in Example 1 was given, and to another group of the mice (n=18), water containing 0.5 wt % of the chitosan oligosaccharide acetate prepared in Example 2 was given. All of the chitin oligosaccharide-ingesting group, the chitosan oligosaccharide acetate-ingesting group and the non-ingesting group (n=21), were grown until 30 weeks old, during which the blood glucose level was measured every two weeks, and the average body weight and the average ingested amounts of the feed and water were measured every week.

Figure 5:
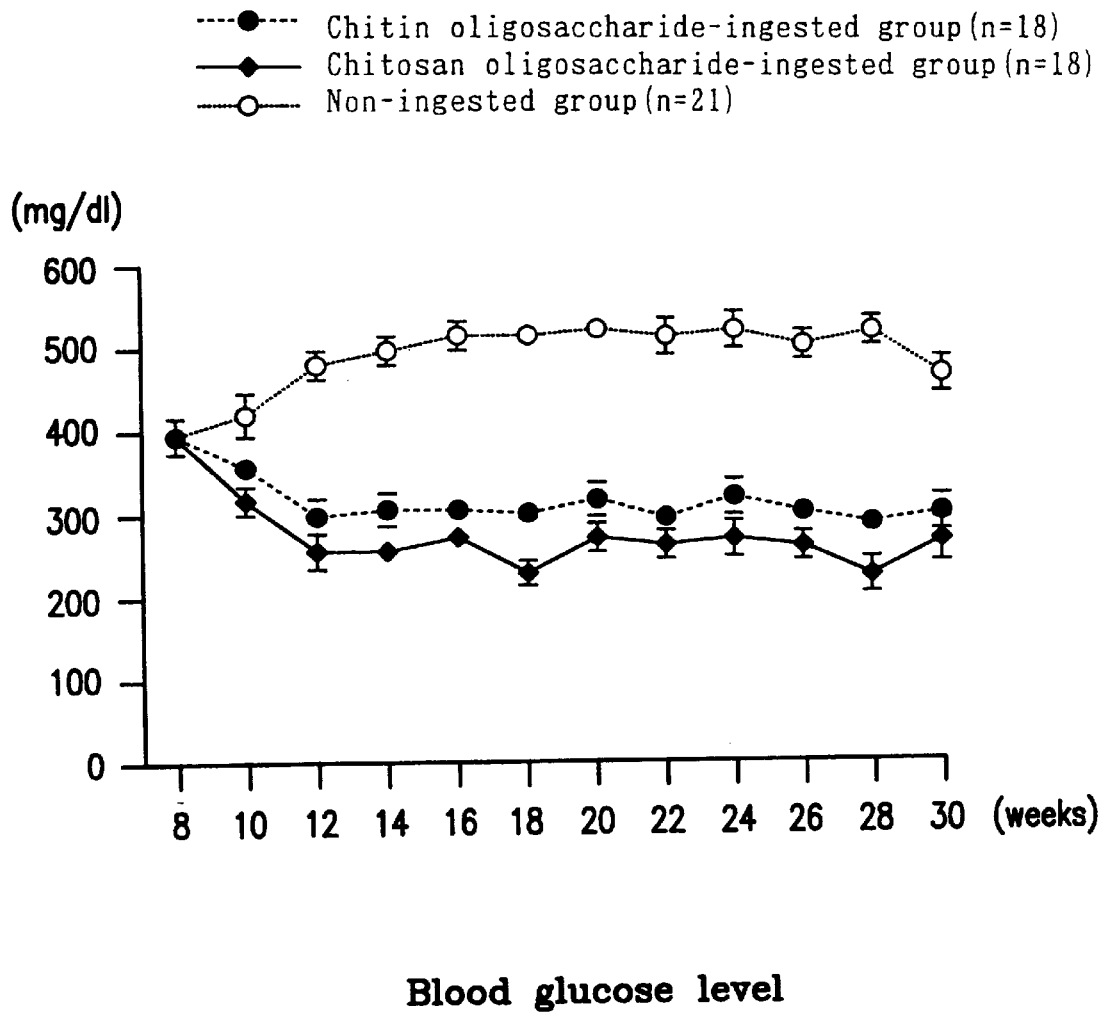
FIG. 5 is a graph showing the change of the blood glucose level in Test Example 2 wherein the effects of chitin oligosaccharide or chitosan oligosaccharide administration on the non insulin dependent diabetes mellitus of mice were examined.
Figure 6:
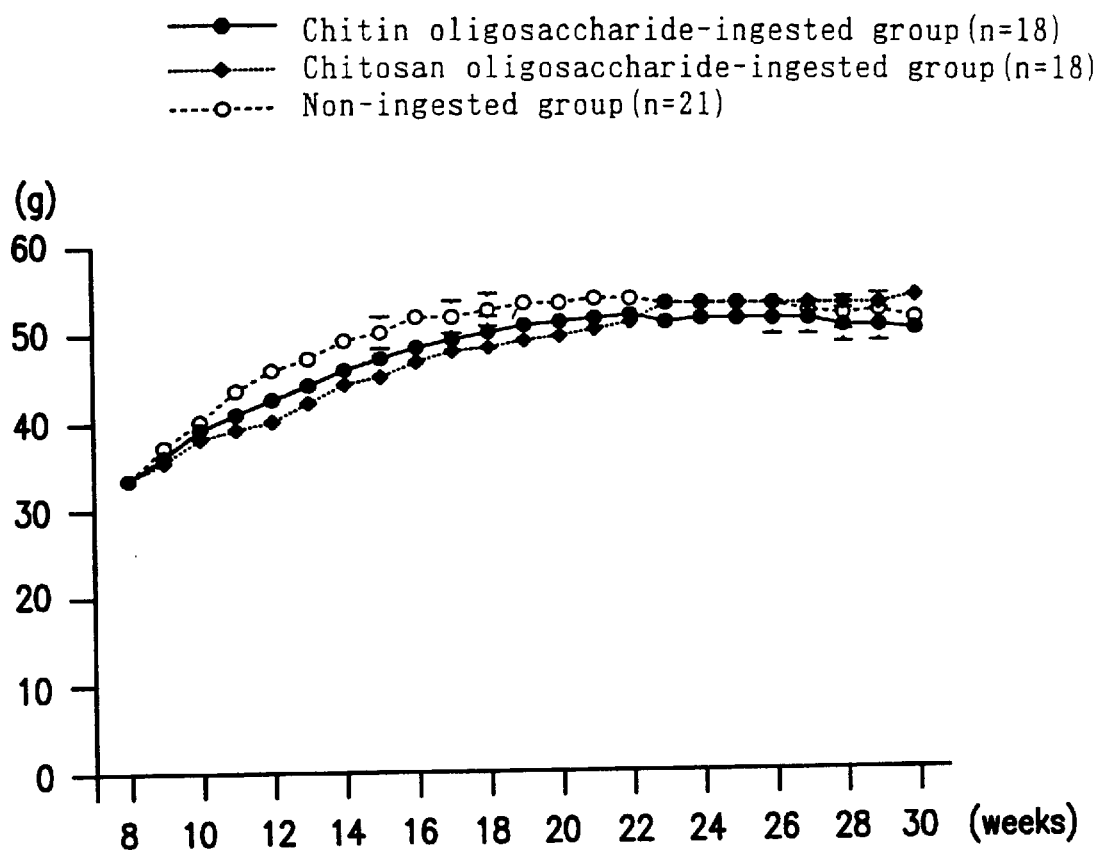
FIG. 6 is a graph showing the change of the body weight in Test Example 2.
Figure 7:
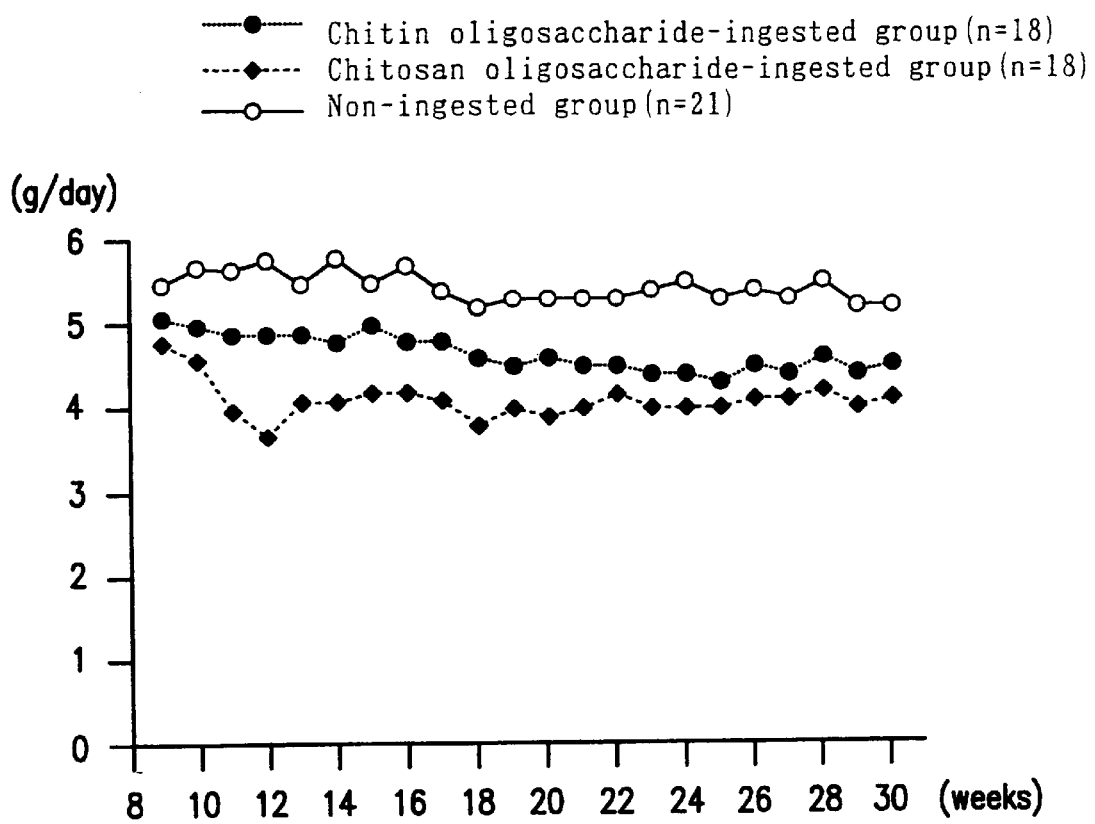
FIG. 7 is a graph showing the change of the ingested amount of feed in Test Example 2.
Figure 8:
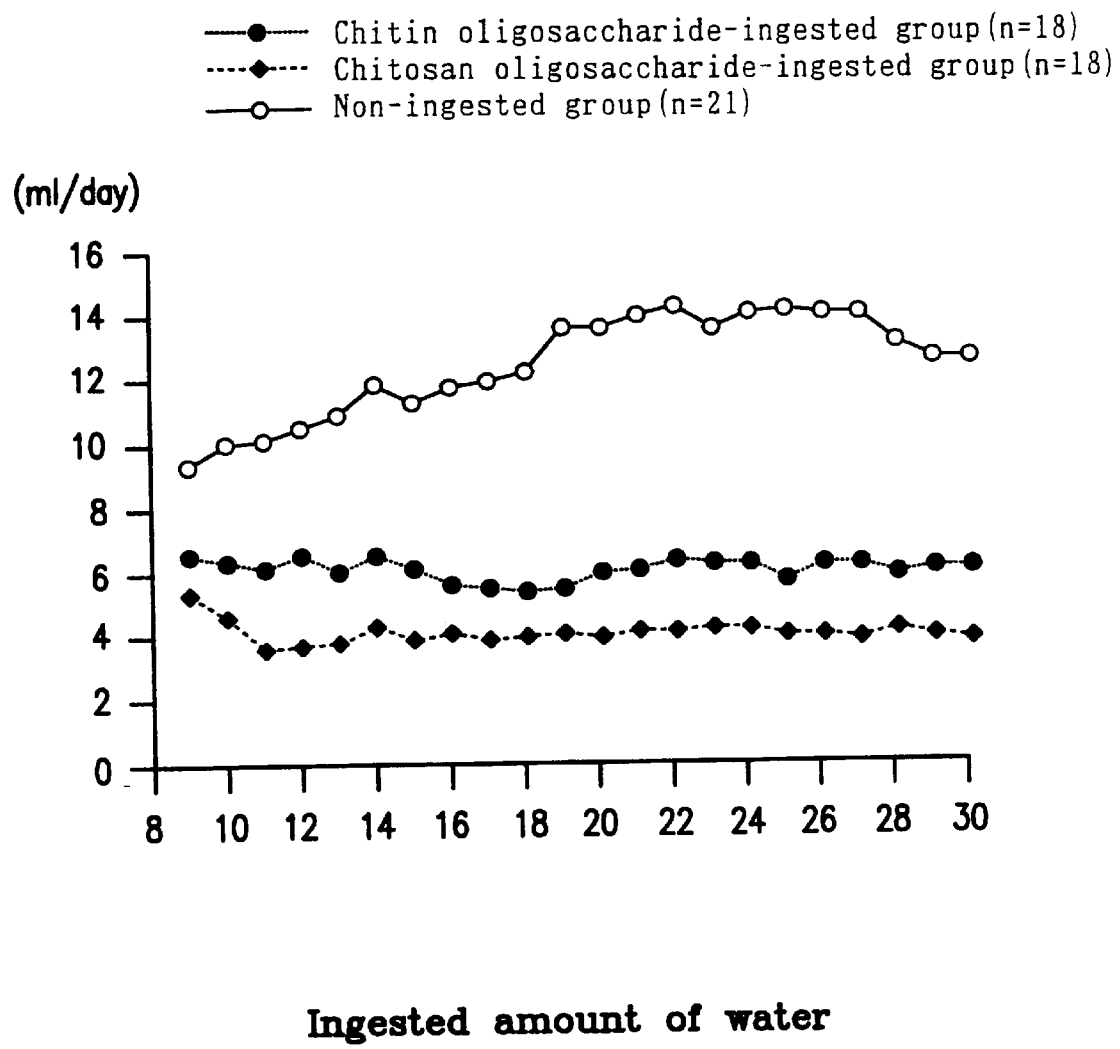
FIG. 8 is a graph showing the change of the ingested amount of water in Test Example 2.

Further, the tissue image of pancreas of 30 weeks old, was inspected. FIG. 5 shows the change of the blood glucose level, FIG. 6 shows the change of the average body weight, and FIGS. 7 and 8 show the change of the average ingested amounts of the feed and water, respectively.

The results are as follows:

(1) Blood glucose level:

The blood glucose levels of the chitin oligosaccharide-ingesting group and the chitosan oligosaccharide acetate-ingesting group, changed at a significantly low level from 12 to 30 weeks old (p<0.01) as compared with the blood glucose level of the non-ingesting group, as shown in FIG. 5. Especially until 18 weeks old, the blood glucose level of the non-ingesting group shows the tendency of increase, whereas the blood glucose level of the chitosan oligosaccharide acetate-ingesting group shows the tendency of decrease.

(2) Average body weight:

The average body weight of the chitosan oligosaccharide acetate-ingesting group changed at a low level until 22 weeks old as shown in FIG. 6. (Significance was admitted at the age of 11, 12, 15 and 16 weeks old (p<0.05)). The average body weight of the non-ingesting group showed the tendency of decrease after 22 weeks old, while the chitosan oligosaccharide acetate-ingesting group showed the tendency of increase, whereby the average body weights of these groups were substantially the same at 30 weeks old. On the other hand, the average body weight of the chitin oligosaccharide-ingesting group changed at a low level (significance was admitted at 11, 12, 15 and 16 weeks old (p<0.05)). However, after 22 weeks old, the average body weight of the non-ingesting group showed the tendency of decrease and was thereby substantially the same as that of the chitosan oligosaccharide acetate-ingesting group at 30 weeks old.

(3) Average ingested amounts of feed and water:

The average ingested amounts of feed and water of the chitin oligosaccharide-ingesting group and the chitosan oligosaccharide acetate-ingesting group, were suppressed as compared with the non-ingesting group during the period between 9 to 30 weeks old (FIGS. 7 and 8). Especially the average ingested amount of water was remarkably suppressed.

TEST EXAMPLE 3

(Preparatory Experiment Concerning the Induced-hepatitis of Mice)

To each of mice (BDF1) of 8 weeks old, fungi of *Corynebacterium parvum* were intravenously administered in an amount of 0.5 mg/mouse, and 7 days later, a lipopolysaccharide (LPS) extracted from *Escherichia coli* was intravenously administered in an amount of 0.1 mg, 1 mg or 10 mg/mouse. Then, each group was inspected by the 21st day, and sacrificed to investigate the condition of hepatitis. The results are shown in Table 1.

TABLE 1

| Dose of LPS | Conditions of mice | Degree of hepatitis |
| --- | --- | --- |
| 10 mg | All mice died in the 8th or 9th day | Not detected |
| 1 mg | 50% died by the 14th day | Potent hepatitis induced |
| 0.1 mg | All mice survived until the 21st day | Weak hepatitis induced |

If fungi of corynebacterium is intravenously administered and, one week later, LPS is intravenously administered, gangrene of liver cells occurs and hepatitis is induced. It has been believed that this is because amacrophage is placed in the primed condition with the corynebacterium (a condition liable to react to stimulation). This method has been established as a liver disorder model from the old time. Further, the mouse (BDF1) is a cross first generation mouse obtained by mating a female of C57BL mouse and a male of DBA/2 mouse.

TEST EXAMPLE 4

(Effects of Chitin Oligosaccharide or Chitosan Oligosaccharide Administration on Experimental Acute Hepatitis)

0.1 mg/mouse of LPS was administered to mice by injection to induce acute hepatitis as described in TEST EXAMPLE 3, and one week later (at the 14th day from the initiation of the test), the chitin oligosaccharide mixture obtained in EXAMPLE 1 or the chitosan oligosaccharide acetate mixture obtained in EXAMPLE 3, was added to water in an amount of 0.5 mg/ml, respectively, and the mice were permitted to freely ingest it. At the 28th day, the mice were sacrificed, and a part of the liver was taken out and subjected to histopathological inspection. Namely, assuming that the colony of lymphoblast is a lesion portion (unit), the number of the units in a section of the liver was counted and the number of the colonies of the lymphoblast in one unit was counted to evaluate the size of the lesion. The results of the test are shown in Table 2.

TABLE 2

| No. of sample | | The number of lesions | The number of lymphoblast in the largest lesion portion |
|---|---|---|---|
| Control group | 1 | 26 | 31 |
| | 2 | 42 | 101 |
| | 3 | 45 | 79 |
| | 4 | 41 | 45 |
| | 5 | 45 | 56 |
| | 6 | 22 | 39 |
| | 7 | 25 | 34 |
| Group to which chitosan oligo-saccharide acetate mixture (EXAMPLE 3) was administered | 8 | 27 | 41 |
| | 9 | 26 | 44 |
| | 10 | 22 | 72 |
| | 11 | 19 | 20 |
| | 12 | 24 | 38 |
| | 13 | 12 | 28 |
| | 14 | 26 | 30 |
| Group to which chitin oligo-saccharide mixture (EXAMPLE 1) was administered | 15 | 26 | 44 |
| | 16 | 37 | 50 |
| | 17 | 29 | 48 |
| | 18 | 17 | 39 |
| | 19 | 10 | 60 |
| | 20 | 10 | 44 |

Table 2 shows the number of the lesions found in a section of the liver of each mouse and the number of the lymphoblast found in the largest lesion. As evident from the results, as compared with the control group to which water was simply given, the group to which the chitin oligosaccharide mixture was administered and the group to which the chitosan oligosaccharide acetate mixture was administered, show lessened number of lesions, whereby the effects for improving the hepatitis are observed.

Further, photographs of typical liver sections of respective groups were taken by an optical microscope (trade name: "Olympus Vanox", manufactured by Olympus Kogaku Kogyo K.K.). The optical microscopic photographs showing tissue images are shown in FIGS. 9(a) to 11(b).

Figure 9A:
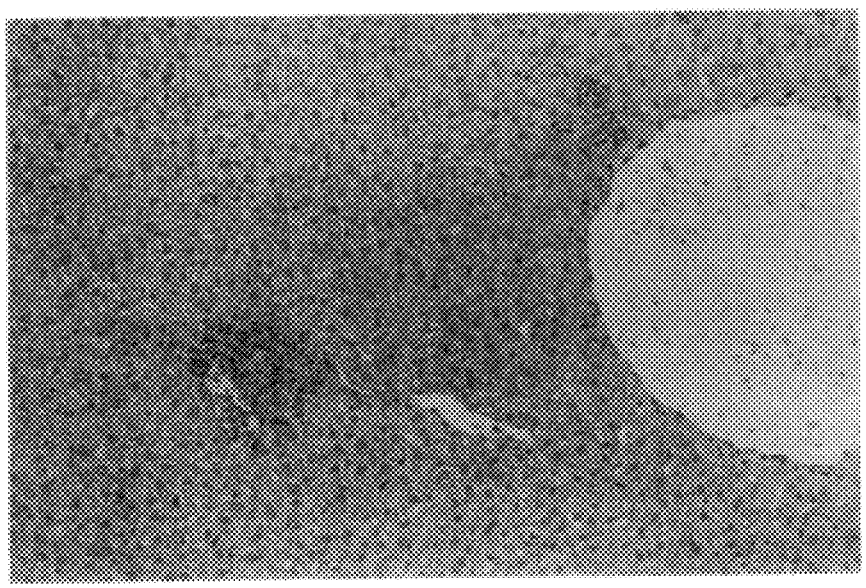
FIG. 9($a$) is a microscopic photograph showing a liver tissue of a mouse of a control group in an experiment of induced hepatitis using mice, with magnification of 100 times.
Figure 9B:
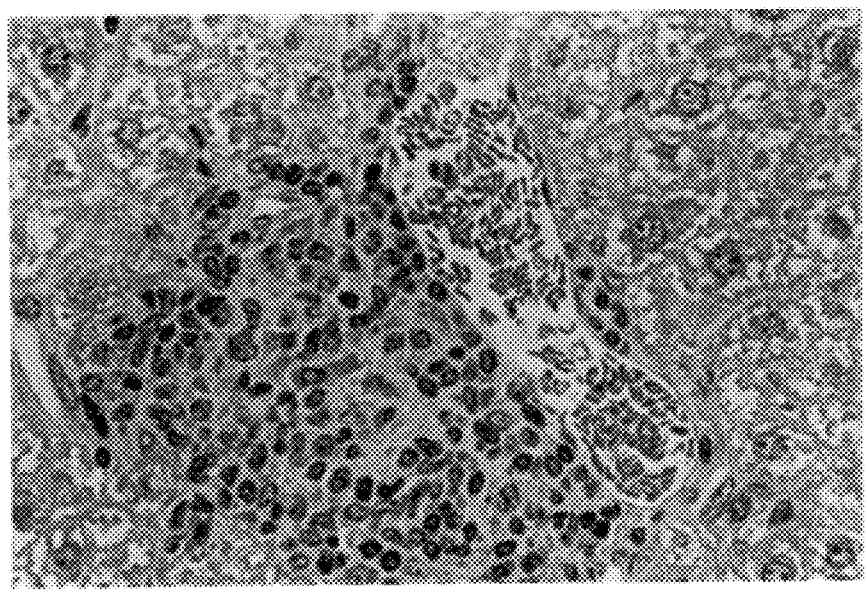

FIGS. 9(a) and 9(b) show the control group. FIG. 9(a) is a microscopic photograph with magnification of 100 times. FIG. 9(b) is a microscopic photograph with magnification of 400 times.

Figure 10A:
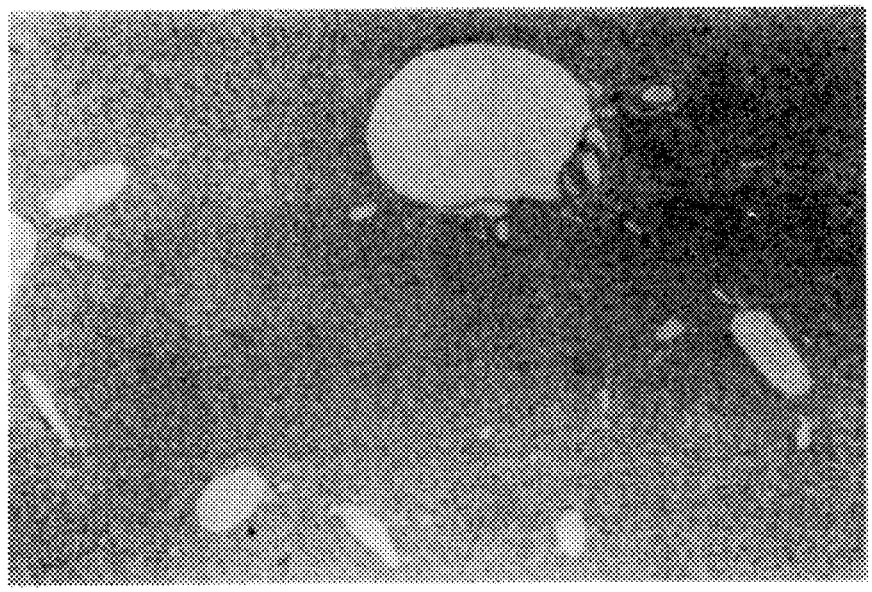
FIG. 10($a$) is a microscopic photograph showing a liver tissue of a mouse of a group to which a chitin oligosaccharide mixture was administered in an experiment of induced hepatitis using mice, with magnification of 100 times.
Figure 10B:
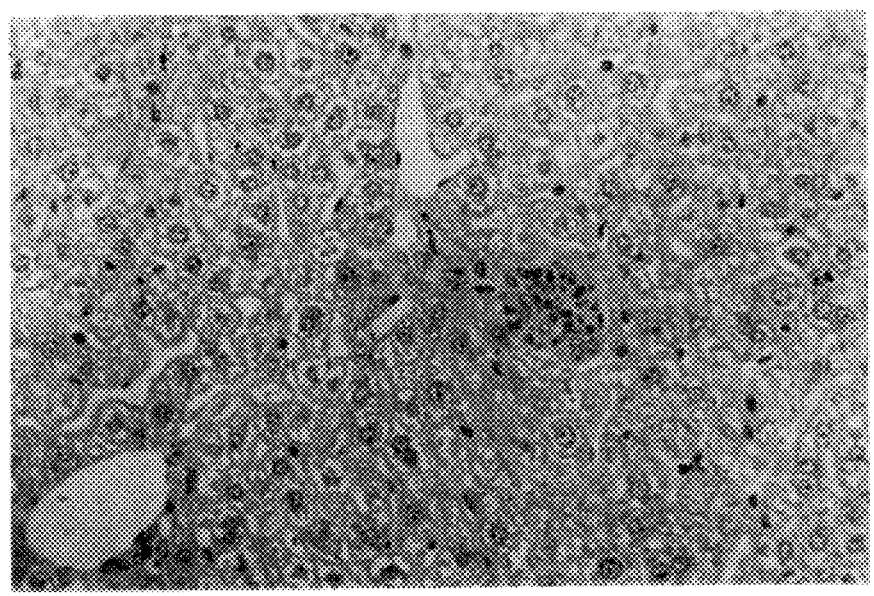

FIGS. 10(a) and 10(b) show the group to which a chitin oligosaccharide mixture (Example 1) was administered. FIG. 10(a) is a microscopic photograph with magnification of 100 times. FIG. 10(b) is a microscopic photograph with magnification of 400 times.

Figure 11A:
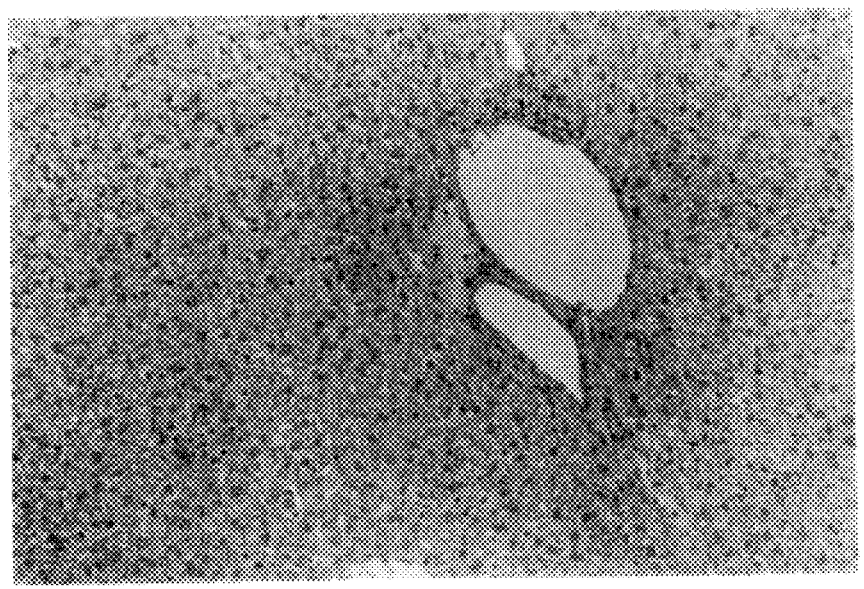
FIG. 11($a$) is a microscopic photograph showing a liver tissue of a mouse of a group to which a chitosan oligosaccharide acetate mixture was administered in an experiment of induced hepatitis using mice, with magnification of 100 times.
Figure 11B:
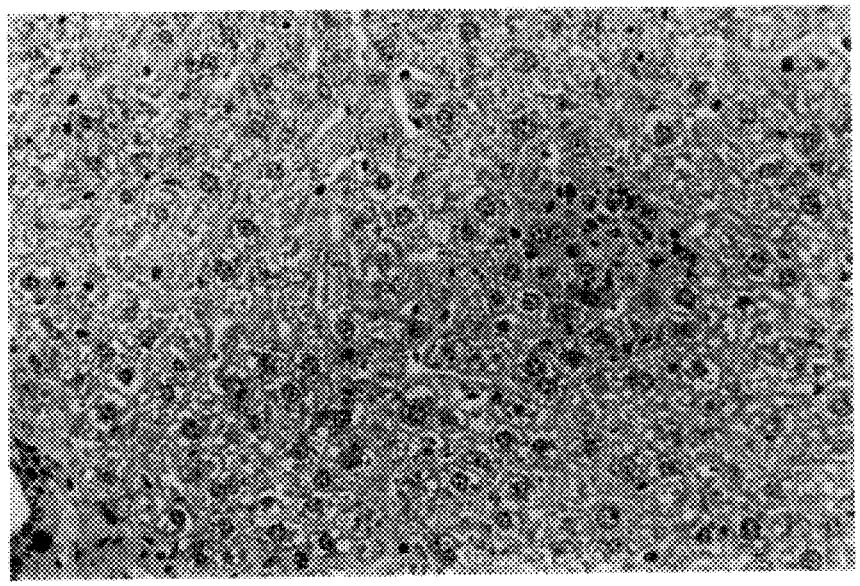

FIGS. 11(a) and 11(b) show the group to which a chitosan oligosaccharide acetate mixture (Example 3) was administered. FIG. 11(a) is a microscopic photograph with magnification of 100 times. FIG. 11(b) is a microscopic photograph with magnification of 400 times.

From these photographs also, as compared with the control group to which water was simply given, the group to which the chitin oligosaccharide mixture was administered and the group to which the chitosan oligosaccharide acetate mixture was administered, show lessened number of lesions, whereby the effects for improving the hepatitis are observed.

What is claimed is:

1. A method for treating non-insulin dependent diabetes which comprises administering a therapeutically effective amount of at least one compound selected from the group consisting of chitin oligosaccharide, chitosan oligosaccharide, and pharmaceutically acceptable salts thereof to a patient in need of such treatment.

2. The method according to claim 1, wherein the chitin oligosaccharide is one or a mixture of chitin oligosaccharide with a degree of polymerization of from 2 to 7 and the chitosan oligosaccharide is one or a mixture of chitosan oligosaccharides with a degree of polymerization of from 2 to 8.

* * * * *